United States Patent [19]

Renner

[11] Patent Number: 4,562,241
[45] Date of Patent: Dec. 31, 1985

[54] DIURETHANE DIUREAS AND THE USE THEREOF

[75] Inventor: Alfred Renner, Muntelier, Switzerland

[73] Assignee: Ciba-Geigy Corporation, Ardsley, N.Y.

[21] Appl. No.: 657,869

[22] Filed: Oct. 4, 1984

[51] Int. Cl.⁴ .................. C08G 59/44; C08G 59/46; C08G 59/48
[52] U.S. Cl. .................. 528/99; 525/504; 528/119; 528/361; 528/369; 560/25; 560/26; 560/158
[58] Field of Search .......... 525/504; 528/119, 99, 528/361, 369; 560/25, 26, 158

[56] References Cited

U.S. PATENT DOCUMENTS

| | | | |
|---|---|---|---|
| 3,386,955 | 6/1968 | Nawakowski et al. | 528/119 X |
| 3,386,956 | 6/1968 | Nawakowski et al. | 528/119 X |
| 3,717,612 | 2/1973 | Babayan | 528/119 |
| 4,110,309 | 8/1978 | Schulze et al. | 528/119 |
| 4,283,520 | 8/1981 | Moser et al. | 528/93 |
| 4,436,890 | 3/1984 | Kaufman | 528/119 X |

Primary Examiner—Earl Nielsen
Attorney, Agent, or Firm—Luther A. R. Hall

[57] ABSTRACT

Diurethane diureas of the formula

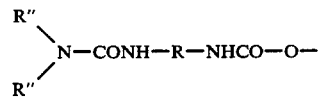

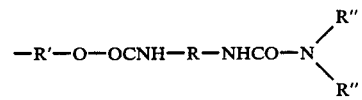

wherein each R is a radical derived from a diisocyanate and having at most 20 C atoms, R' is a radical derived from a diol and having a molecular weight of at most 1500, and the radicals R'' are each methyl or ethyl, or both radicals R'' bound to the same N atom form together with the N atom the piperidino, morpholino or pyrrolidino radical, are valuable curing agents for epoxide resins, and are also suitable as accelerators for the hot-curing of epoxide resins with dicyandiamide, cyanoacetyl compounds and polycarboxylic acid anhydrides.

10 Claims, No Drawings

DIURETHANE DIUREAS AND THE USE THEREOF

The present invention relates to novel diurethane diureas, to the use thereof in curable epoxide resin mixtures, and to the products obtained from these mixtures by curing.

The use of specific mono-, di- and polyureas as curing agents for epoxide resins is known from the U.S. Pat. No. 3,386,956. These prior known curable epoxide resin mixtures are in general stable in storage at room temperature, but on being cured they leave much to be desired with regard to reactivity.

The object of the invention was to provide epoxide resin mixtures which would have a high level of latency and rapidly cure at elevated temperature. It has been found that certain diurethane diurea compounds largely satisfy these requirements, and can be used both as curing agents and as curing accelerators.

The present invention thus relates to diurethane diureas of the formula I $$\begin{array}{c} R'' \\ \diagdown \\ N-CONH-R-NHCO-O- \\ \diagup \\ R'' \end{array} \qquad (I)$$

$$-R'-O-OCNH-R-NHCO-N \begin{array}{c} \diagup R'' \\ \diagdown R'' \end{array}$$

wherein
R is in each case a radical derived from a diisocyanate and having at most 20 C atoms,
R' is a radical derived from a diol and having a molecular weight of at most 1500, and the radicals
R" are each methyl or ethyl, or both radicals R" bound to the same N atom form together with the N atom the piperidino, morpholino or pyrrolidino radical.

The meanings of the symbols in formula I are preferably as follows:
R is in each case a radical of an aromatic diisocyanate,
R' is a radical of an aliphatic diol or of a polyalkylene glycol, and
R" is in each case methyl or ethyl.

Particularly interesting diurethane diureas of the formula I are those wherein:
R is in each case phenylene or methylphenylene,
R' is hexamethylene or the radical of a polyethylene or polypropylene glycol having a molecular weight of at most 500, and
R" is in each case methyl.

The radicals R derived from diisocyanates can be aliphatic, cycloaliphatic, aromatic or araliphatic radicals. The aliphatic radicals R can be straight-chain or branched-chain. The aromatic and cycloaliphatic radicals R can optionally contain substituents that are not reactive to epoxide resins, for example halogen atoms, —NO$_2$ and C$_1$-C$_4$-alkyl, preferably methyl, or C$_1$-C$_4$-alkoxy.

Diisocyananates containing a radical R are for example: ethylenediisocyanate, tetramethylene-1,4-diisocyanate, hexamethylene-1,6-diisocyanate, dodecane-1,12-diisocyanate, isomeric mixtures of 2,2,4- and 2,4,4-trimethylhexamethylenediisocyanate, cyclobutane-1,3-diisocyanate, cyclohexane-1,3- and -1,4-diisocyanate, and also any chosen mixtures of these isomers, hexahydrotoluylene-2,4- and -2,6-diisocyanate, perhydro-2,4'- or -4,4-diphenylmethanediisocyanate, 3-isocyanatomethyl-3,5,5-trimethylcyclohexylisocyanate ("isophoronediisocyanate"), arylenediisocyanates, which can be substituted by C$_1$-C$_4$-alkyl, such as m- and p-phenylenediisocyanate, naphthylenediisocyanates, diphenylmethane-4,4'-diisocyanate, methylphenylenediisocyanate, such as 2,4- and 2,6-methylphenylenediisocyanate and mixtures thereof, diisopropylbenzenediisocyanates, aralkyldiisocyanates, such as 1-(isocyanatophenyl)-ethylisocyanate or m- and p-xylylenediisocyanate, as well as polyisocyanates of the above-mentioned types substituted by various groups, for example by C$_1$-C$_4$-alkoxy, phenoxy (wherein phenyl can be substituted by C$_1$-C$_4$-alkyl), NO$_2$ or Cl. The aromatic diisocyanates are preferred, for example 2,4- and 2,6-toluylenediisocyanate, and also any mixtures of these isomers, diphenylmethane-4,4'-diisocyanate and m- and p-phenylenediisocyanate.

The radicals R' derived from diols can be aliphatic, cycloaliphatic and/or araliphatic radicals having OH groups bound to nonaromatic C atoms. The aliphatic radicals can be straight-chain or branched-chain, and can also be interrupted by one or more sulphur or oxygen atoms, preferably by oxygen atoms. Diols containing a radical R' are for example glycols, such as ethylene glycol, propylene glycol, butane-1,4-diol, neopentyl glycol, hexane-1,6-diol, thiodiethylene glycol, the ether alcohols, such as di- or triethylene glycol, di- or tripropylene glycol, the higher poly(oxyethylene)- and poly-(oxypropylene)glycols, oxyethylated or oxypropylated bisphenols or hydantoins, such as are obtained, in a known manner, by an addition reaction of ethylene oxide or propylene oxide with these compounds; perhydrobisphenols, such as bis-(4-hydroxycyclohexyl)-methane and 2,2-bis-(4-hydroxycyclohexyl)propane, 1,1-bis-(hydroxymethyl)-3-cyclohexane or cyclohexane-1,3-diol and -1,4-diol.

The compounds of the formula I according to the invention can be produced by reacting, in a first stage, a diisocyanate of the formula II $$OCN-R-NCO \qquad (II)$$

with a diol of the formula III $$HO-R'-OH \qquad (III),$$

in the molar ratio of 2:1, to a diisocyanatodiurethane of the formula IV $$OCN-R-NHCO-O-R'-O-OCN-H-R-NCO \qquad (IV);$$

and then, in a second stage, reacting the diisocyanatodiurethane with a secondary amine of the formula V $$HN \begin{array}{c} \diagup R'' \\ \diagdown R'' \end{array} , \qquad (V)$$

wherein R, R' and R" are as defined under the formula I, in the molar ratio of 1:2, to obtain a diurethane diurea of the formula I.

In the case of the secondary amines of the formula V, these are, according to definition, dimethylamine, diethylamine, methylethylamine, piperidine, morpholine and pyrrolidine. Readily volatile or gaseous secondary amines, for example dimethylamine, are advantageously used in excess.

The reaction of the diisocyanate of the formula II with a diol of the formula III can be performed using customary methods for producing urethanes. The reaction can be carried out at room temperature or at elevated temperature, and in the presence or absence of organic solvents or of catalysts. Suitable solvents are for example toluene or dioxane, and suitable catalysts are for example tert-amines.

As mentioned at the commencement, the diurethane diureas according to the invention are valuable curing agents and curing accelerators in curable epoxide resin mixtures. The diurethane diureas exhibit good compatibility with epoxide resins and can be easily processed therewith. Forming further subject matter of the invention are therefore also hot-curable mixtures which contain
(a) an epoxide resin and
(b) an effective amount of a diurethane diurea of the formula I.

When the epoxide resin mixtures according to the invention contain the diurethane diureas of the formula I in an amount sufficient for curing, that is, as curing agents, there are present in the curable mixture in general 5 to 25, preferably 10 to 20, parts by weight of (b) per 100 parts by weight of epoxide resin (a).

In the mixtures according to the invention, the epoxide resins (a) preferably used are those having at least two glycidyl or β-methylglycidyl groups bound directly to an oxygen, nitrogen or sulfur atom or atoms. Mentioned as examples of such resins are the polyglycidyl- and poly-(β-methylglycidyl)esters, which can be obtained by reaction of a compound containing two or more carboxylic acid groups per molecule with epichlorohydrin, glycerol dichlorohydrin or β-methylepichlorohydrin in the presence of an alkali. These polyglycidyl esters can be derived from aliphatic polycarboxylic acids, for example from oxalic acid, succinic acid, glutaric acid, adipic acid, pimelic acid, suberic acid, azelaic acid, sebacic acid or dimerised or trimerised linoleic acid; from cycloaliphatic polycarboxylic acids, such as tetrahydrophthalic acid, 4-methyltetrahydrophthalic acid, hexahydrophthalic acid and 4-methylhexahydrophthalic acid; as well as from aromatic polycarboxylic acids, such as phthalic acid, isophthalic acid and terephthalic acid.

Further examples are polyglycidyl- and poly-(β-methylglycidyl)ethers, which are obtainable by reaction of a compound containing at least two free alcoholic and/or phenolic hydroxyl groups per molecule with the corresponding epichlorohydrin under alkaline conditions; or also in the presence of an acid catalyst with a subsequent alkali treatment. These ethers can be produced from acyclic alcohols, such as ethylene glycol, diethylene glycol and higher poly-(oxyethylene)-glycols, propane-1,2-diol and poly-(oxypropylene)-glycols, propane-1,3-diol, butane-1,4-diol, poly-(oxytetramethylene)glycols, pentane-1,5-diol, hexane-1,6-diol, hexane-2,4,6-triol, glycerol, 1,1,1-trimethylpropane, pentaerythritol, sorbitol and polyepichlorohydrins; from cycloaliphatic alcohols, such as resorcitol, quinitol, bis-(4-hydroxycyclohexyl)-methane, 2,2-bis-(4-hydroxycyclohexyl)-propane and 1,1-bis(hydroxymethyl)-3-cyclohexane; and from alcohols having aromatic nuclei, such as N,N-bis-(2-hydroxyethyl)-aniline and p,p'-bis-(2-hydroxyethylamino)-diphenylmethane.

They can also be produced from novolaks formed from mononuclear phenols, such as resorcinol and hydroquinone, and from polynuclear phenols, such as bis-(4-hydroxyphenyl)-methane, 4,4'-dihyroxydiphenyl, bis-(4-hydroxyphenyl)-sulfone, 1,1,2,2-tetrakis-(4-hydroxyphenyl)-ethane, 2,2-bis-(4-hydroxyphenyl)-propane and 2,2-bis-(3,5-dibromo-4-hydroxyphenyl)-propane; and also from aldehydes, such as formaldehyde, acetaldehyde, chloral and furfurol with phenols, such as phenol itself, and phenol ring-substituted by chlorine atoms or alkyl groups each having up to 9 carbon atoms, such as 4-chlorophenol, 2-methylphenol and 4-tert-butylphenol.

Poly-(N-glycidyl) compounds embrace for example those which are obtained by dehydrochlorination of the reaction products of epichlorohydrin with amines containing at least two aminohydrogen atoms, such as aniline, n-butylamine, bis-(4-aminophenyl)-methane, m-xylyenediamine and bis-(4-methylaminophenyl)-methane; triglycidylisocyanurate, as well as N,N'-diglycidyl derivatives of cyclic alkyleneureas, such as ethyleneurea and 1,3-propyleneurea; and hydantoins, such as 5,5-dimethylhydantoin.

Poly-(S-glycidyl) compounds are for example the di-S-glycidyl derivatives of dithiols, such as ethane-1,2-dithiol and bis-(4-mercaptomethylphenyl)ether.

Also suitable are for example epoxide resins in which the glycidyl groups are bound to hetero atoms of varying nature, for example the N,N,O-triglycidyl derivative of 4-aminophenol, of glycidyl ethers/glycidyl esters of salicylic acid, N-glycidyl-N'-(2-glycidyloxypropyl)-5,5-dimethylhydantoin and 2-glycidyloxy-1,3-bis-(5,5-dimethyl-1-glycidylhydantoin-3-yl)propane.

Suitable for the hot-curable mixtures according to the invention are also the cycloaliphatic epoxide resins wherein the epoxide group is part of the aliphatic ring system, for example bis-(2,3-epoxycyclopentyl)ether, 2,3-epoxycyclopentyl-glycidyl ether and 1,2-bis-(2,3-epoxycyclopentyloxy)-ethane.

A mixture of epoxide resins can if desired be used.

Preferred epoxide resins are polyglycidyl ethers, polyglycidyl esters and poly-(N-glycidyl) derivatives of aromatic amines. Specially preferred resins are the polyglycidyl ethers of 2,2-bis-(4-hydroxyphenyl)-propane, bis-(4-hydroxyphenyl)-methane, or of a novolak formed from formaldehyde and phenol, or phenol ring-substituted by a chlorine atom or an alkyl having 1 to 4 C atoms, and having a 1,2-epoxide content of at least 0.5 equivalent per kilogram; bis-(4-(diglycidylamino)-phenyl)-methane and p-(diglycidylamino)-phenyl-glycidyl ether.

It has also been found that the diurethane diureas of the formula I according to the invention are moreover valuable accelerators in the hot-curing of epoxide resins with hot-curing agents, preferably dicyandiamide, cyanoacetyl compounds and polycarboxylic acid anhydrides.

Further subject matter is hence formed by hot-curable mixtures according to the invention which additionally contain (c) a large amount by weight, relative to the amount by weight of the diurethane diurea (b), of the dicyandiamide, of a cyanoacetyl compound of the formula VI

wherein R''' is a radical derived from an n-valent alcohol or n-valent amine and having a partial molecular weight of ≦2000, and n is a number from 1 to 4, or of a polycarboxylic acid anhydride.

The cyanoacetyl compounds of the formula VI and the use thereof as curing agents for epoxide resins are known from the U.S. Pat. No. 4,283,520, and, as is stated therein, the cyanoacetyl compounds are used, in curable epoxide resin mixtures, in such amounts that to one cyanoacetyl group there are 3 to 4 epoxide groups. Dicyandiamide and the polycarboxylic acid anhydrides are used in the customary amounts for curing agents.

In the curable epoxide resin mixtures according to the invention which contain the component (b) as the accelerator, the diurethane diurea compounds (b) are in general used in amounts of 0.1 to 10 parts by weight, preferably 1 to 5 parts by weight, per 100 parts by weight of epoxide resin.

Suitable cyanoacetyl compounds of the formula VI are for example; neopentyl glycol-bis-cyanoacetic acid ester, cyanoacetic acid-N-isobutylamide, ethylene glycol-bis-cyanoacetic acid ester, 1,4-cyclohexanedimethanol-bis-cyanoacetic acid ester and cyanoacetic acid-N-(N-dimethylaminopropylamide).

The polycarboxylic acid anhydrides employed are preferably the customary aliphatic, cycloaliphatic or aromatic polycarboxylic acid anhydrides suitable for curing epoxide resins, for example phthalic anhydride, tetrahydrophthalic anhydride, hexahydrophthalic anhydride, dodecylsuccinic anhydride, hexachloroendomethylenetetrahydrophthalic anhydride and endomethylenetetrahydrophthalic anhydride and mixtures thereof, maleic anhydride, succinic anhydride, pyromellitic anhydride, benzophenone-3,3'-4,4'-tetracarboxylic dianhydride, polysebacic anhydride and polyazelaic anhydride, as well as isophthalic anhydride, terephthalic anhydride, citric anhydride or mellitic anhydride.

The curable mixtures according to the invention can also contain plasticisers, such as dibutyl phthalate, dioctyl phthalate or tricresyl phosphate, or additives such as extenders, fillers, reinforcing agents, colouring agents, flow-promoting agents and mould release agents. Suitable extenders, fillers and reinforcing agents are for example: asbestos, asphalt, bitumen, glass fibres, textile fibres, carbon or boron fibres, mica, alumina, gypsum, titanium dioxide, chalk, quartz flour, cellulose, kaolin, ground dolomite, wollastonite, siliceous earth having a large specific surface (obtainable under the trade-name of "Aerosil"), alumina modified with long-chain amines (obtainable under the trade-name of "Bentone"), powdered polyvinyl chloride, polyolefin or aminoplasts, metal powders, such as aluminium or iron powders. Also fireproofing agents, such as antimony oxide, can be added to the curable mixtures.

The curable compositions according to the invention can be used as laminating, impregnating and casting resins, powder coatings, moulding compounds, bonding cements and sealing compounds, embedding and insulating compounds for the electrical industry, but particularly as adhesives and priming for adhesives.

The compositions according to the invention are preferably cured by heating them to a temperature within the range of 100° to 180° C., especially 100° to 140° C. A heating time of 30 to 120 minutes usually suffices for curing.

The following Examples further illustrate the invention. Parts are parts by weight.

EXAMPLE 1

Preparation of

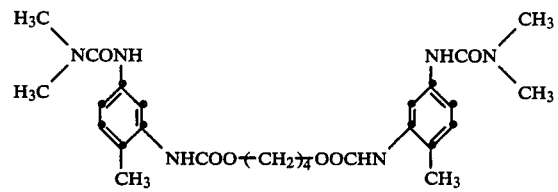

348 parts by weight of toluylene-2,4-diisocyanate are diluted with 400 parts of toluene; the temperature is then raised to 80° C. and 90 parts of butanediol-1,4 are added with vigorous stirring. The toluene is afterwards distilled off in vacuo; 350 parts of dioxane are added, and 200 parts of gaseous dimethylamine are subsequently introduced at 22°-25° C. Excess dimethylamine and dioxane is then removed at 140° C. and 19.9 mbar in a rotary evaporator. There are thus obtained 519.6 parts (98.3% of theory) of a pale yellow solid resin having a glass transition temperature ($T_G$) of 73.5° C.

| Analysis | calculated for $C_{26}H_{36}N_6O_6$ | found |
|---|---|---|
| % C: | 59.08 | 59.4 |
| % H: | 6.86 | 7.1 |
| % N: | 15.91 | 15.6 |

EXAMPLE 2

Preparation of

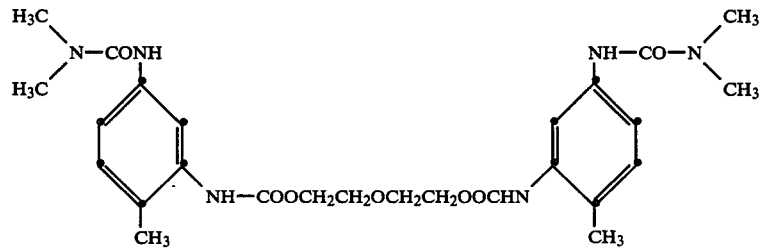

The procedure is carried out as in Example 1 except that 106.1 parts of diethylene glycol are added dropwise in place of butanediol-1,4. Introduction of dimethylamine: 320 parts.

Yield: 533 parts (98% of theory)

$T_G$: 75.5° C.

| Analysis: | calculated for $C_{26}H_{36}N_6O_7$ | found |
|---|---|---|
| % C: | 57.34 | 57.4 |
| % H: | 6.66 | 7.0 |
| % N: | 15.43 | 15.5 |

EXAMPLE 3

Preparation of

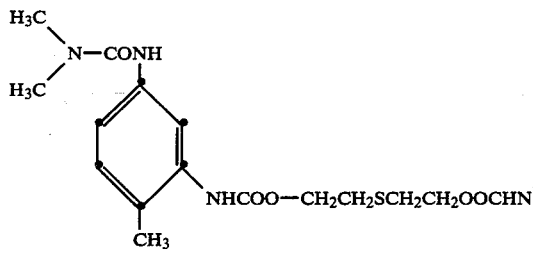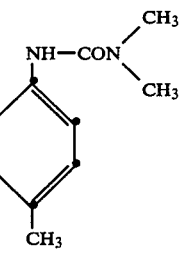

| Starting: materials | toluylene-2,4-diisocyanate | 348 parts |
|---|---|---|
|  | thio-diethylene glycol | 122.2 parts |
|  | toluene | 500 parts |
|  | dioxane | 350 parts |
|  | dimethylamine | 250.2 parts |

Procedure as in Example 1.
Yield: 536 parts (95.7% of theory)
$T_G$: 81° C.

| Starting: materials | toluylene-2,4-diisocyanate | 348 parts |
|---|---|---|
|  | triethylene glycol | 150 parts |
|  | toluene | 400 parts |
|  | dioxane | 350 parts |
|  | dimethylamine | 200 parts |

Procedure as in Example 1.
yield: 570 parts (97% of theory) of a pale yellow solid resin $T_G$: 67° C.

| Analysis: | calculated for $C_{28}H_{40}N_6O_8$ | found |
|---|---|---|
| % C | 57.13 | 57.0 |
| % H | 6.85 | 6.9 |
| % N | 14.28 | 14.2 |

EXAMPLE 5

Preparation of

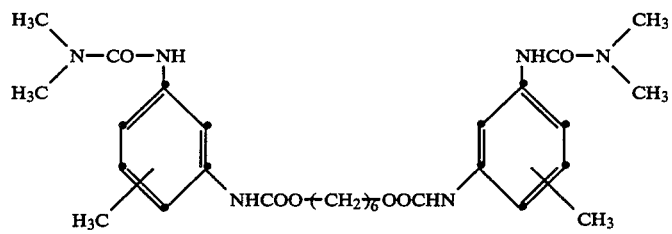

| Starting: materials | Desmodur T ® (commercial mixture of 2,4- and 2,6-toluylenediisocyanate; commercially obtainable product of BAYER AG): | 348 parts |
|---|---|---|
|  | toluene | 500 parts |
|  | dioxane | 350 parts |
|  | dimethylamine | 171 parts |

Procedure as in Example 1.
Yield: 535.2 parts of a yellow solid resin (96.3%)

| Analysis: | calculated for $C_{26}H_{36}N_6O_6S$ | found |
|---|---|---|
| % C: | 55.69 | 55.5 |
| % H: | 6.47 | 6.6 |
| % N: | 14.98 | 14.7 |
| % S: | 5.71 | 5.7 |

EXAMPLE 4

Preparation of

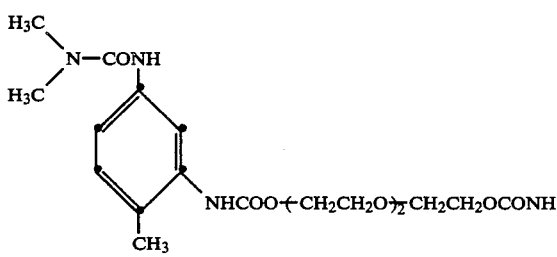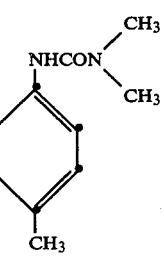

T_G: 75° C.

| Analysis: | calculated for $C_{28}H_{40}N_6O_6$ | found |
|---|---|---|
| % C | 60.48 | 59.7 |
| % H | 7.58 | 7.3 |
| % N | 15.11 | 14.8 |

EXAMPLE 6

Preparation of

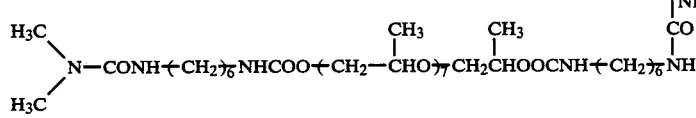

| Starting: materials | hexamethylene-1,6-diisocyanate | 168 parts |
|---|---|---|
| | polypropylene glycol 425 | 212.5 parts |
| | toluene | 300 parts |
| | dioxane | 300 parts |
| | dimethylamine | 86.7 parts |

Procedure as in Example 1. There are obtained 410 parts of a partially crystalline, wax-like substance (96.4% of theory) having a nitrogen content of 10.2% (calculated 9.87%).

EXAMPLE 7

Preparation of

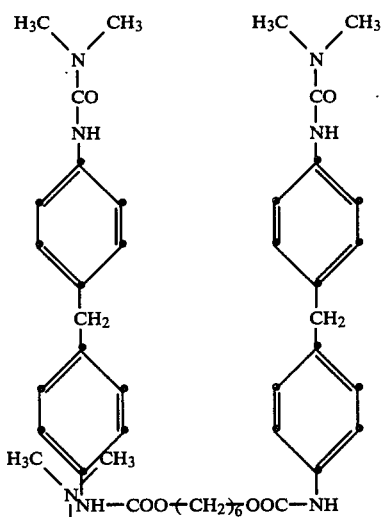

| starting: materials | diphenylmethane-4,4'-diisocyanate | 218 parts |
|---|---|---|
| | hexanediol-1,6 | 51.5 parts |
| | toluene | 300 parts |
| | dioxane | 300 parts |
| | dimethylamine | 62 parts |

Procedure as in Example 1.
Yield: 301 parts (97.5% of theory)
T_G: 163° C.

| Analysis: | calculated for $C_{40}H_{48}N_6O_6$ | found |
|---|---|---|
| % C | 67.78 | 68.4 |
| % H | 6.83 | 6.6 |
| % N | 11.86 | 11.2 |

EXAMPLE 8

Preparation of

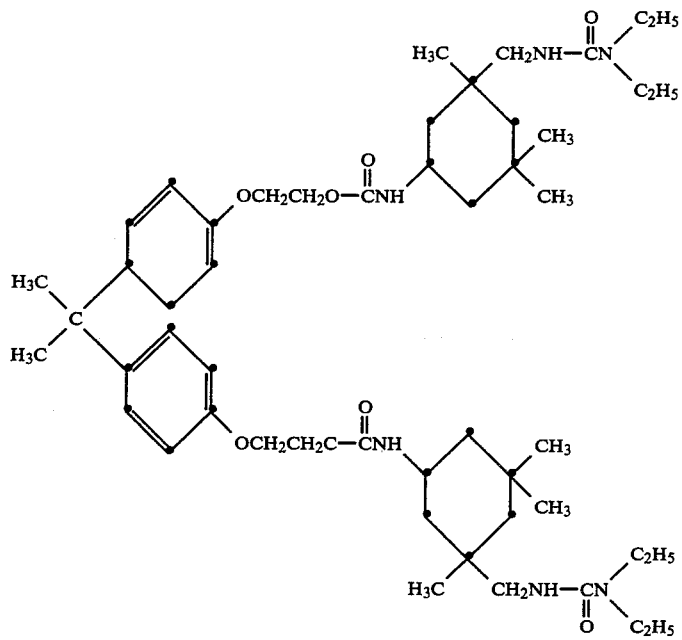

158 parts of 2,2-bis-[4-(2-hydroxyethyl)phenoxy]-propane are dissolved in 500 parts of toluene, and this solution is added dropwise at 85°–90° C., with stirring, to 222.27 parts of isophorone-diisocyanate. The mixture is allowed to subsequently react for 2 hours, and 73.14 parts of diethylamine are then introduced. After further reaction for 2 hours at 90° C., the toluene is removed in vacuo at 150° C. in a rotary evaporator. There are obtained 359 parts of a solid resin (79.2% of theory) having a glass transition temperature of 90.5° C.

| Analysis: | calculated for $C_{45}H_{82}N_6O_8$ | found |
|---|---|---|
| % C | 66.63 | 67.15 |
| % H | 9.36 | 9.18 |
| % N | 9.52 | 9.26 |

EXAMPLE 9

Preparation of

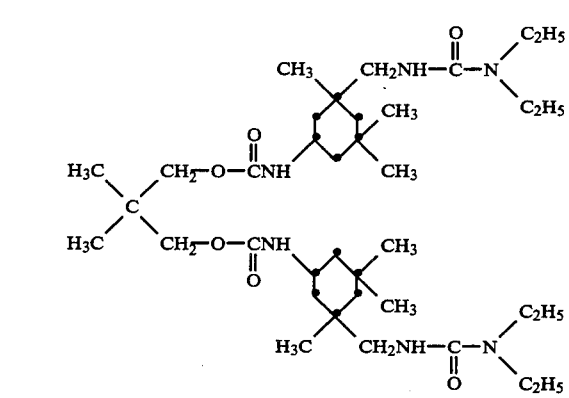

| Starting: materials | isophorone-diisocyanate | 222.27 parts |
|---|---|---|
| | neopentyl glycol | 52.07 parts |
| | toluene | 400 parts |
| | diethylamine | 73.14 parts |

Procedure as in Example 8.
yield: 327.2 parts, corresponding to 94.2% of theory.

| Analysis: | calculated for $C_{37}H_{70}N_6O_6$ | found |
|---|---|---|
| % C | 63.94 | 63.54 |
| % H | 10.15 | 10.17 |
| % N | 12.09 | 11.98 |
| $T_G$: | 72° C. | |

EXAMPLE 10

Preparation of

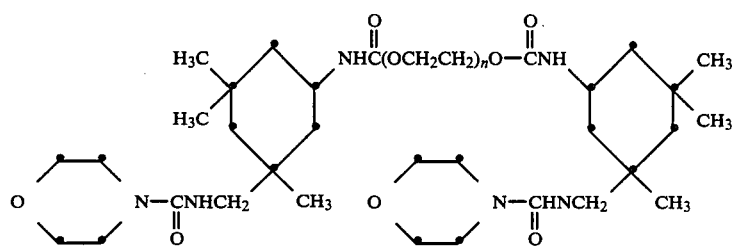

| Starting: | isophorone-diisocyanate | 222.27 parts |
| --- | --- | --- |
| materials | polyeopentyl glycol 1000 | 2.50 parts |
|  | toluene | 500 parts |
|  | morpholine | 43.56 parts |

Procedure as in Example 8.

yield: 502 parts of a yellow viscous resin, corresponding to 97.3% of theory.

| Analysis: | found |
| --- | --- |
| % C | 57.12 |
| % H | 8.58 |
| % N | 5.26 |

APPLICATION EXAMPLES (A) Curing of an epoxide resin with diurethane diurea resins In each case, 85 parts of an epoxide resin based on bisphenol-A having an epoxide content of 5.1–5.5 val/kg and a viscosity of 9000–13000 mPa.s (epoxide resin I) are mixed with 15 parts of each of the diurethane diureas produced in Examples 1 to 5. The gelling times of these mixtures and the properties of the moulded materials obtained from these mixtures by curing (2 hours at 100° C. and 8 hours at 140° C.) are given in the following Table.

| Curing agent according to Example | Gelling time at 120° C. | Flexural[1] strength N/mm² | Impact[2] bend strength kJ/m² | Dimensional[3] stability under heat °C. | Cold water absorption after 4 days at at 25° C. % | Boiling water absorption after 1 hr at 100° C. % | Tensile[4] shearing strength N/mm² |
| --- | --- | --- | --- | --- | --- | --- | --- |
| 1 | 12 min 10 sec | 68.2 | 4.97 | 104 | 0.31 | 0.62 | 16.5 |
| 2 | 13 min 2 sec | 67.8 | 6.77 | 105 | 0.30 | 0.57 | 17.3 |
| 3 | 13 min 20 sec | 66.3 | 4.91 | 105 | 0.30 | 0.61 | 17.3 |
| 4 | 16 min 11 sec | 80.5 | 15.21 | 99 | 0.32 | 0.72 | 17.5 |
| 5 | 14 min 20 sec | 51.2 | 3.92 | 108 | 0.27 | 0.50 | 16.5 |

[1]according to DIN 53452
[2]according to DIN 53455
[3]according to DIN 53453
[4]according to DIN 53283

(B) Acceleration of the dicyandiamide curing of an epoxide resin

|  | Gelling time at 120° C. |
| --- | --- |
| 12 parts of epoxide resin I | >18 hours |

1.33 parts of dicyandiamide
and additionally

| | | Gelling time at 120° C. |
| --- | --- | --- |
| 0.266 | part of diurethane diurea according to Example 1: | 13.0 min. |
| 0.266 | part of diurethane diurea according to Example 2: | 10.67 min. |
| 0.266 | part of diurethane diurea according to Example 3: | 13.15 min. |
| 0.266 | part of diurethane diurea according to Example 4: | 13.0 min. |
| 0.266 | part of diurethane diurea according to Example 5: | 10.83 min. |
| 0.266 | part of diurethane diurea according to Example 6: | 33.63 min. |
| 0.266 | part of diurethane diurea according to Example 7: | 46.68 min. |
| 0.266 | part of diurethane diurea according to Example 8: | 71 min. |
| 0.266 | part of diurethane diurea according to Example 9: | 69 min. |
| 0.266 | part of diurethane diurea according to Example 10: | 265 min. |

(C) Acceleration of the cyanoacetyl curing of an epoxide resin

| | Gelling time at 120° C. |
| --- | --- |
| 8.45 parts of epoxide resin I<br>1.55 parts of NC—CH$_2$—CONH—CH$_2$CH(CH$_3$)CH$_3$ | >16 hours | and additionally

| 0.2 | part of diurethane diurea according to Example 1: | 31.0 min. |
| --- | --- | --- |
| 0.2 | part of diurethane diurea according to Example 2: | 34.35 min. |
| 0.2 | part of diurethane diurea according to | 31.50 min. |

-continued

|  | | Gelling time at 120° C. |
|---|---|---|
| 0.2 | part of diurethane diurea according to Example 3: | 33.13 min. |
| 0.2 | part of diurethane diurea according to Example 4: | 30.07 min. |
| 0.2 | part of diurethane diurea according to Example 5: | 82.5 min. |
| 0.2 | part of diurethane diurea according to Example 6: | 176.3 min. |
| 0.2 | part of diurethane diurea according to Example 7: | 187 min. |
| 0.2 | part of diurethane diurea according to Example 8: | 177.5 min. |
| 0.2 | part of diurethane diurea according to Example 9: | 339 min. |
| 0.2 | part of diurethane diurea according to Example 10: |  |

(D) Acceleration of the anhydride curing of an epoxide resin 8.0 parts of epoxide resin I are mixed with 5.51 parts of cis-hexahydrophthalic anhydride. This mixture has a gelling time of 674 minutes at 120° C.

If there is added in each case to such a mixture 0.27 part (2%) of each of the diurethane diureas according to Examples 1–10, there are obtained the following results:

| Curable mixture containing | Gelling time at 120° C. |
|---|---|
| diurethane diurea according to Example 1: | 88 min. |
| diurethane diurea according to Example 2: | 88 min. |
| diurethane diurea according to Example 3: | 105 min. |
| diurethane diurea according to Example 4: | 129 min. |
| diurethane diurea according to Example 5: | 111 min. |
| diurethane diurea according to Example 6: | 77 min. |
| diurethane diurea according to Example 7: | 14 min. |
| diurethane diurea according to Example 8: | 62 min. |
| diurethane diurea according to Example 9: | 112 min. |
| diurethane diurea according to Example 10: | 73 min. |

The storage stability of the curable mixtures catalysed with the diurethane diureas according to Examples 1–10 is only slightly reduced.

(E) Curing of N,N,N′,N′-tetraglycidyl-4,4′-diaminodiphenylmethane

N,N,N′,N′-Tetraglycidyl-4,4′-diaminodiphenylmethane having an epoxide equivalent weight of 133 (epoxide resin II) and the diurethane diurea produced in Example 5 are mixed together in the mixture ratios given in the following Table, and subsequently cured. The curing conditions (hours (h)/°C.) and the properties of the moulded materials obtained are likewise shown in the Table.

TABLE

| Example | E 1 | E 2 | E 3 | E 4 |
|---|---|---|---|---|
| Epoxide resin II (g) | 95 | 90 | 85 | 80 |
| diurethane diurea according to Example 5 (g) | 5 | 10 | 15 | 20 |
| gelling (h/°C.) | 2/90 | | | |
| curing (h/°C.) | 40/140 + 6/190 | | | |
| glass transition temperature (°C.) | 140 | 193 | 231 | 239 |
| flexural strength (N/mm²) | 47 | 31 | 54 | 38 |
| impact bend strength (kJ/m²) | 2.0 | 1.0 | 2.0 | 1.6 |
| cold water absorption 4 days at 25° C. (%) | 0.33 | 0.57 | 0.68 | 1.31 |
| hot water absorption 1 hour at 100° C. (%) | 0.41 | 0.38 | 0.47 | 1.87 |

What is claimed is:
1. A diurethane diurea of the formula I

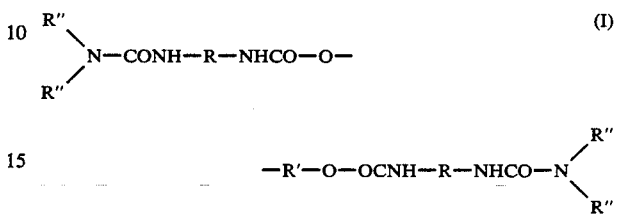

wherein
R is in each case a radical derived from a diisocyanate and having at most 20 C atoms,
R′ is a radical derived from a diol and having a molecular weight of at most 1500, and the radicals
R″ are each methyl or ethyl, or both radicals R″ bound to the same N atom form together with the N atom the piperidino, morpholino or pyrrolidino radical.

2. A diurethane diurea according to claim 1, wherein in the formula I
R is in each case a radical of an aromatic diisocyanate,
R′ is a radical of an aliphatic diol or of a polyalkylene glycol, and
R″ is in each case methyl or ethyl.

3. A diurethane diurea according to claim 1, wherein in the formula I
R is in each case phenylene or methylphenylene,
R′ is hexamethylene or the radical of a polyethylene or polypropylene glycol having a molecular weight of at most 500, and
R″ is in each case methyl.

4. A process for producing a diurethane diurea of the formula I according to claim 1, which process comprises reacting, in a first stage, a diisocyanate of the formula II

with a diol of the formula III

in the molar ratio of 2:1, to a diisocyanate diurethane of the formula IV

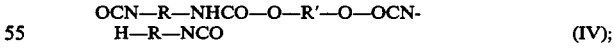

and then, in a second stage, reacting the diisocyantodiurethane with a secondary amine of the formula V

wherein R, R′ and R″ are as defined under the formula I, in the molar ratio of 1:2, to obtain a diurethane diurea of the formula I.

5. A hot-curable mixture which contains (a) an epoxide resin and
(b) an effective amount of a diurethane diurea of the formula I according to claim 1.

6. A mixture according to claim 5 which contains 5 to 25 parts by weight of (b) per 100 parts by weight of (a).

7. A mixture according to claim 5, which additionally contains (c) a large amount by weight, relative to the amount by weight of (b), of the dicyandiamide, of a cyanoacetyl compound of the formula VI

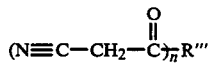
(VI)

wherein R''' is a radical derived from an n-valent alcohol or n-valent amine and having a partial molecular weight of $\leqq 2000$, and n is a number from 1 to 4, or of a polycarboxylic acid anhydride.

8. A mixture according to claim 5, wherein (a) contains at least two glycidyl or $\beta$-methylglycidyl groups which are bound directly to an oxygen, nitrogen or sulfur atom or atoms.

9. A mixture according to claim 5, wherein (a) is a polyglycidyl ether, a polyglycidyl ester or a poly(N-glycidyl) derivative of an aromatic amine.

10. The products obtained by the hot-curing of a mixture according to claim 5.

* * * * *